United States Patent
Sullivan et al.

(10) Patent No.: US 9,295,427 B2
(45) Date of Patent: Mar. 29, 2016

(54) FILTERING PATIENT SIGNAL ALSO FOR VENTILATION ARTIFACTS

(71) Applicant: Physio-Control, Inc., Redmond, WA (US)

(72) Inventors: Joseph L. Sullivan, Kirkland, WA (US); Robert G. Walker, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 14/930,631

(22) Filed: Nov. 2, 2015

(65) Prior Publication Data

US 2016/0051202 A1 Feb. 25, 2016

Related U.S. Application Data

(60) Division of application No. 14/032,376, filed on Sep. 20, 2013, now Pat. No. 9,204,845, and a continuation-in-part of application No. 13/676,593, filed on Nov. 14, 2012, now Pat. No. 9,084,545.

(60) Provisional application No. 61/704,932, filed on Sep. 24, 2012.

(51) Int. Cl.
| | |
|---|---|
| *A61B 5/0402* | (2006.01) |
| *A61B 5/00* | (2006.01) |
| *A61B 5/04* | (2006.01) |
| *A61B 5/053* | (2006.01) |
| *A61N 1/39* | (2006.01) |

(52) U.S. Cl.
CPC ............ *A61B 5/7207* (2013.01); *A61B 5/0402* (2013.01); *A61B 5/04017* (2013.01); *A61B 5/053* (2013.01); *A61B 5/7217* (2013.01); *A61B 5/742* (2013.01); *A61N 1/3925* (2013.01)

(58) Field of Classification Search
CPC .. A61B 5/7207; A61B 5/04017; A61B 5/742; A61B 5/7217; A61B 5/053; A61B 5/0402; A61N 1/3925
See application file for complete search history.

(56) References Cited

U.S. PATENT DOCUMENTS

| | | | |
|---|---|---|---|
| 6,752,771 B2 * | 6/2004 | Rothman et al. | 601/44 |
| 2013/0184600 A1 * | 7/2013 | Tan et al. | 600/518 |

* cited by examiner

*Primary Examiner* — Rex R Holmes
(74) *Attorney, Agent, or Firm* — Kavounas Patent Law Office, PLLC

(57) ABSTRACT

In embodiments, an external medical device is intended to care for a patient. If it receives an input that signifies that ventilation artifact is present in a signal of the patient, it transmits a corrective signal responsive to the received input. In further embodiments, a patient signal is received, which is generated from a patient while the patient is or was receiving chest compressions at a frequency Fc, and also receiving ventilations at frequency Fv. At least one filter mechanism may be applied to the patient signal to substantially remove artifacts at a) frequency Fc, b) a higher harmonic of frequency Fc, and c) a third frequency substantially equaling frequency Fc plus or minus frequency Fv, while substantially passing other frequencies between them. As a result, the patient signal can be cleaner, for diagnosing the patient's state more accurately.

22 Claims, 11 Drawing Sheets

DEFIBRILLATION SCENE

FIG. 1  *DEFIBRILLATION SCENE*

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

FIG. 2  *TWO MAIN TYPES OF EXTERNAL DEFIBRILLATORS*

COMPONENTS OF EXTERNAL DEFIBRILLATOR

FIG. 5   *MACHINE FREQUENCIES*

FIG. 6   *ECG SIGNAL OF PATIENT RECEIVING CHEST COMPRESSIONS & VENTILATIONS*

700

| 710 DETECT THAT VENTILATION ARTIFACT IS PRESENT IN PATIENT SIGNAL |

| 720 TAKE CORRECTIVE ACTION |

*METHODS*

| 810 RECEIVE INPUT SIGNIFYING THAT VENTILATION ARTIFACT IS PRESENT IN PATIENT SIGNAL |

| 820 TRANSMIT CORRECTIVE SIGNAL |

*METHODS*

FIG. 8

*FAST FOURIER TRANSFORM OF ECG SIGNAL FROM ASYSTOLIC PATIENT RECEIVING CHEST COMPRESSIONS FROM CONVENTIONAL MECHANICAL CPR DEVICE*

FIG. 9

FAST FOURIER TRANSFORM OF ECG
SIGNAL FROM ASYSTOLIC PATIENT
RECEIVING CHEST COMPRESSIONS FROM
MECHANICAL CPR DEVICE HAVING
PRECISE FREQUENCY CONTROL

FIG. 10

*FREQUENCY RESPONSE OF COMB FILTER TO REMOVE CHEST COMPRESSION ARTIFACTS FROM ECG SIGNAL*

FIG. 11

FREQUENCY RESPONSE OF INVERSE COMB FILTER TO DETECT CHEST COMPRESSION & VENTILATION FREQUENCIES

FIG. 12

FIG. 13  *SAMPLE FILTERED FREQUENCIES*

FIG. 14  *ESTIMATED POWER NOISE SPECTRUM FROM PATIENT RECEIVING CONCURRENTLY CHEST COMPRESSIONS & VENTILATIONS*

FIG. 15

FILTERING PATIENT SIGNAL ALSO FOR VENTILATION ARTIFACTS

CROSS REFERENCE TO RELATED PATENT APPLICATIONS

This patent application is a divisional of co-pending U.S. patent application Ser. No. 14/032,376, filed on Sep. 20, 2013, which claims priority from U.S. Provisional Patent Application Ser. No. 61/704,932, filed on Sep. 24, 2012, and which further is a Continuation-In-Part of U.S. patent application Ser. No. 13/676,593, filed on Nov. 14, 2012 and issued as U.S. Pat. No. 9,084,545 B2, all commonly assigned herewith.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

There are also CPR machines, namely mechanical chest compression devices that will perform CPR on a patient. One example is the LUCAS® device sold by Physio-Control, Inc. For the rescue breathing component of CPR, rescuers may perform manual ventilations for the patient, called "breaths". In addition, there are automatic ventilators that will provide ventilations for the patient. A problem is that the compressions and the ventilations may introduce undesirable artifact in the patient signal, making it harder for machines to diagnose the patient.

BRIEF SUMMARY

The present description gives instances of methods, medical devices, methods of operating such medical devices, systems, and programmed processors to control such medical devices for removing chest artifacts from the signal of a patient who is receiving chest compressions and ventilations.

In embodiments, an external medical device is intended to care for a patient. If it receives an input that signifies that ventilation artifact is present in a signal of the patient, it transmits a corrective signal responsive to the received input.

As a result, the patient signal can be cleaner, either by abating a source of the artifact or by applying a filter to it.

In further embodiments, a patient signal is received, which is generated from a patient while the patient is or was receiving chest compressions at a frequency Fc, and also receiving ventilations at frequency Fv. At least one filter mechanism may be applied to the patient signal to substantially remove artifacts at a) frequency Fc, b) a higher harmonic of frequency Fc, and c) a third frequency substantially equaling frequency Fc plus or minus frequency Fv, while substantially passing other frequencies between them. As a result, the patient signal can be cleaner, for diagnosing the patient's state more accurately.

These and other features and advantages of this description will become more readily apparent from the following Detailed Description, which proceeds with reference to the drawings, in which:

BRIEF DESCRIPTION OF THE DRAWINGS

FIG. 2 is a table listing two main types of the external defibrillator shown in FIG. 1, and who they might be used by.

DETAILED DESCRIPTION

As has been mentioned, the present description is about medical devices, methods of operating such medical devices, systems, and programmed processors to control such medical devices for removing chest artifacts from the signal of a patient who is receiving chest compressions and ventilations.

Embodiments are now described in more detail.

Figure 1:
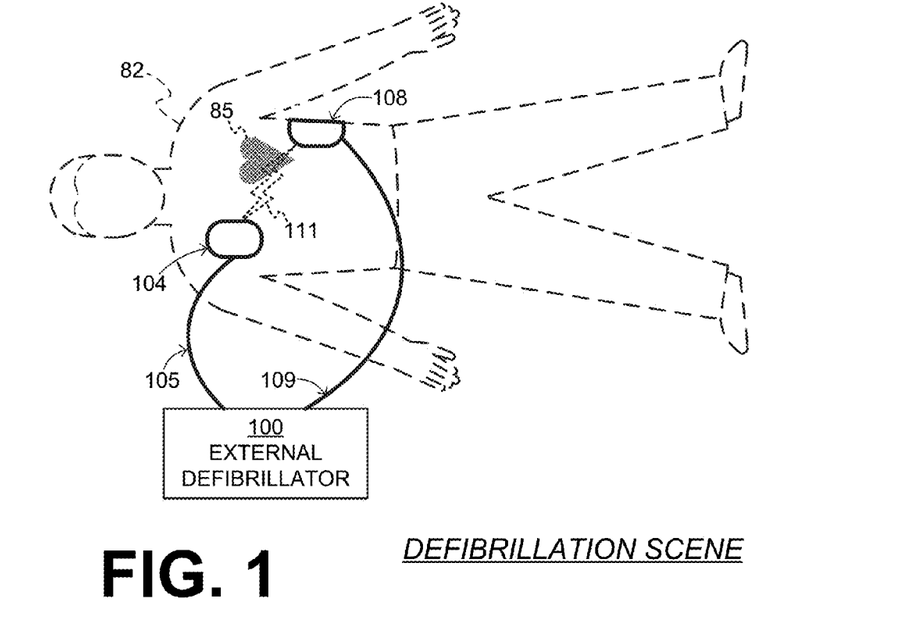
FIG. 1 is a diagram of a scene where an external defibrillator is used to save the life of a person according to embodiments.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

Figure 2:
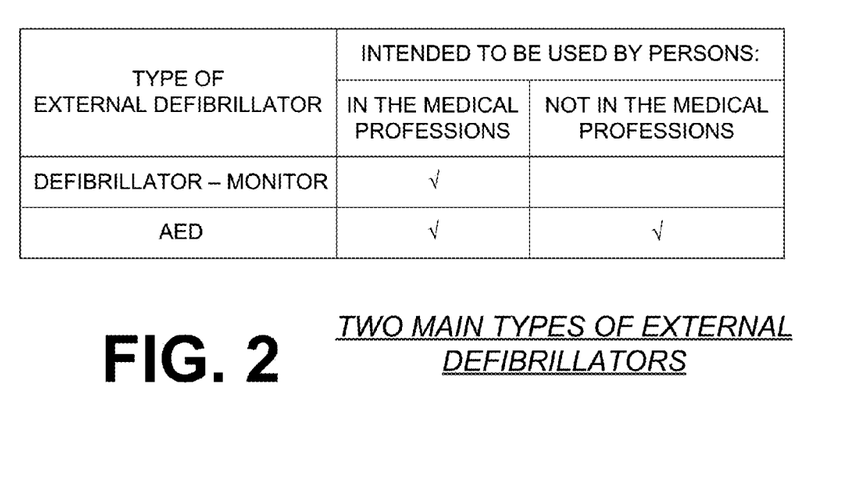

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor.

As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

Figure 3:
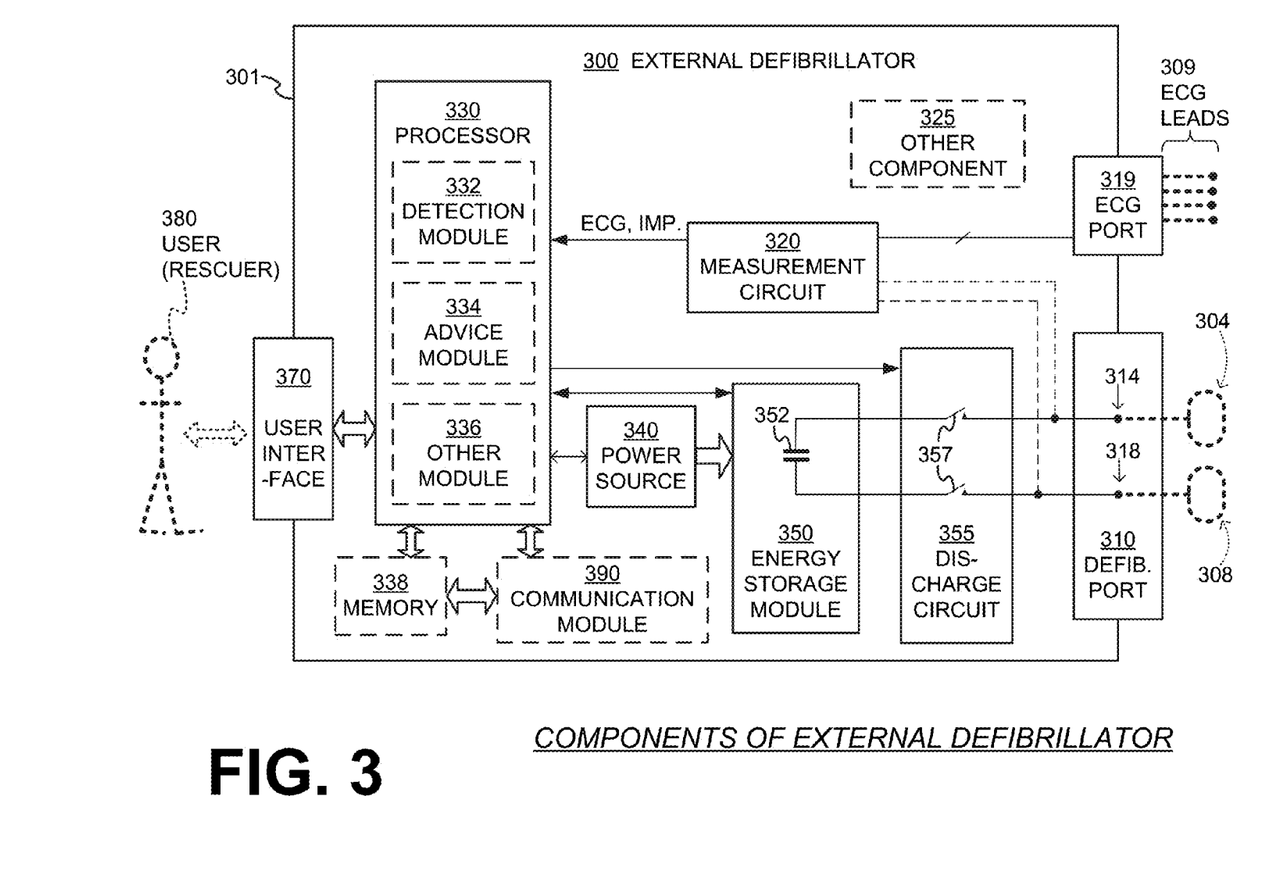
FIG. 3 is a functional block diagram showing components of an external defibrillator, such as the one shown in FIG. 1, which is made according to embodiments.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 structured to filter the ECG signal, e.g., apply at least one filter to the signal so as to remove chest compression artifacts resulting from chest compressions being delivered to the person 82.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways, for causing actions and operations to be performed. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

A feature of a defibrillator can be CPR-prompting. Prompts are issued to the user, visually or by sound, so that the user can administer CPR. Examples are taught in U.S. Pat. No. 6,334,070 and U.S. Pat. No. 6,356,785.

Figure 4:
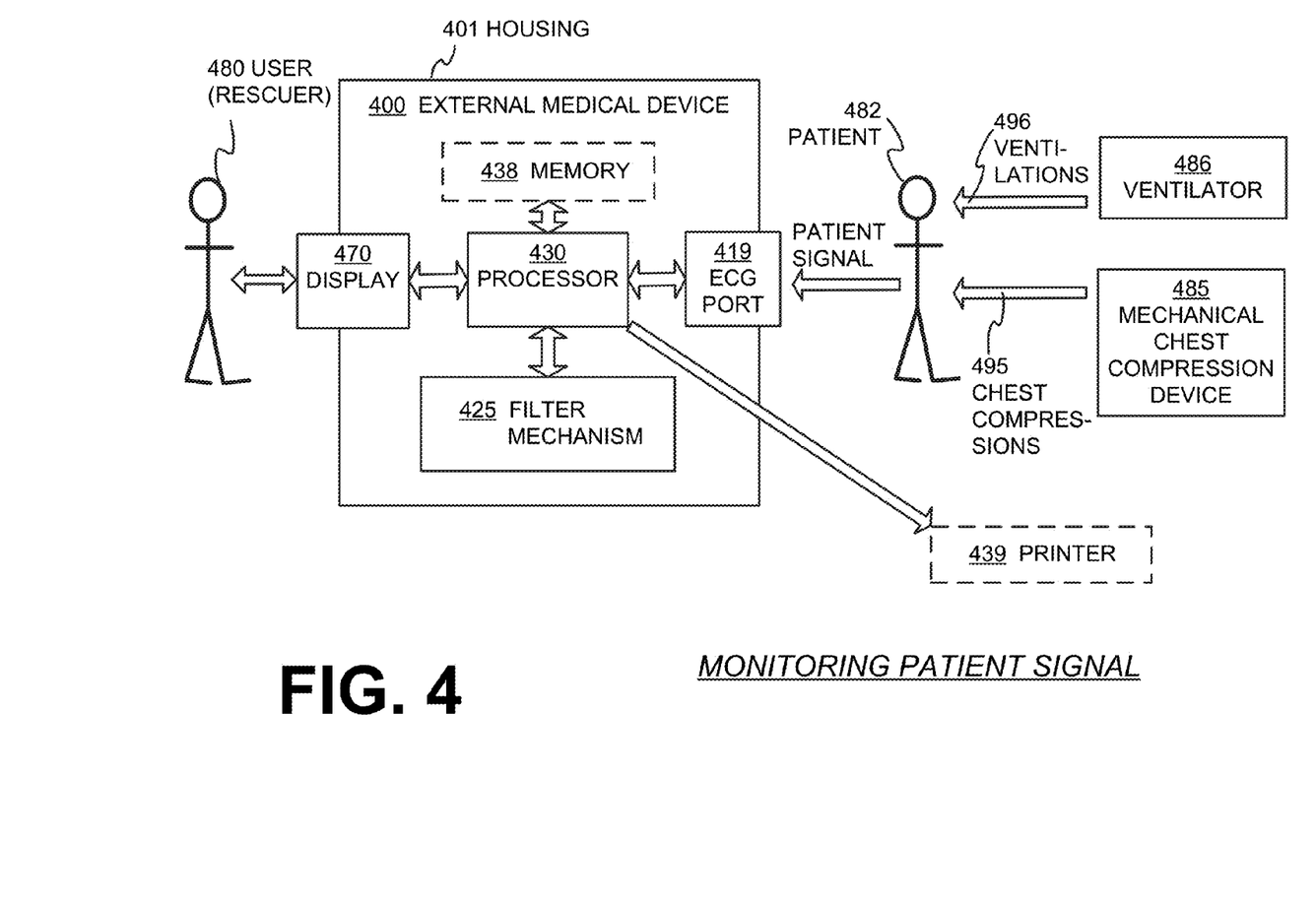
FIG. 4 is a functional block diagram showing monitoring a patient signal according to embodiments.

FIG. 4 is a functional block diagram showing monitoring a patient signal according to embodiments. A mechanical chest compression device 485 delivers chest compressions 495 to patient 482. The compressions are at a nominal frequency Fc. A sample value of Fc is about 100 compressions per minute (1.667 Hz). Mechanical chest compression devices may or may not have substantially precise frequency control. In addition, a ventilator 486 delivers ventilations 496 to patient 482 at a nominal frequency Fv. Ventilator 486 may be an electrical/mechanical device, or it could be a person operating a setup such as a bag-valve mask or a self-inflating bag attached to an endotracheal tube. A sample value of Fv is about 10 ventilations per minute (0.167 Hz).

Figure 5:
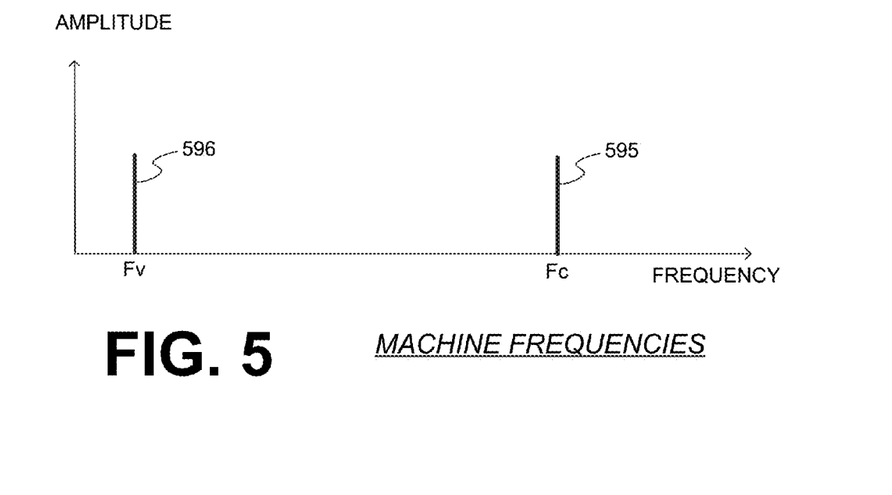
FIG. 5 is a diagram of operating frequencies of machines used in FIG. 4.

FIG. 5 is a diagram of the frequencies of possible machines 485, 486 that can be used in FIG. 4. In the example of FIG. 5, the machines have precise frequency control. A frequency component 595 is contributed at Fc from compressions 495, and a frequency component 596 is contributed at Fv from ventilations 496.

Returning to FIG. 4, an external device 400 is provided, which is preferably also a medical device intended to care for a patient. Device 400 has a housing 401, and an ECG port 419 that can receive a patient signal, such as an ECG signal or an impedance signal. As mentioned above, the patient signal may have artifacts due to compressions 495 and ventilations 496 that patient 482 is receiving.

Device 400 also has a display 470 in connection with the housing 401, and possibly other output devices, such as a speaker, and so on. Display 470 is for use by user/rescuer 480. Device 400 also has, within housing 401, a processor 430 that could be similar to processor 330. Device 400 optionally also has, within housing 401, a memory 438. Memory 438 could be a non-transitory storage medium that stores programs for execution by processor 430. Processor 430 may be further configured to cause the display 470 to visually present, to user 480, a version of the patient signal. The version could be as the signal is received, or as has been filtered as described below. Alternatively, or in addition, the processor 430 may be configured to cause an optional printer 439 to print out the version of the patient signal.

In some embodiments, device 400 also has, within housing 401, a filter mechanism 425. In this example, filter mechanism 425 is shown as separate from processor 430, although equivalently processor 430 can perform the functions of filter mechanism 425 according to embodiments.

Figure 6:
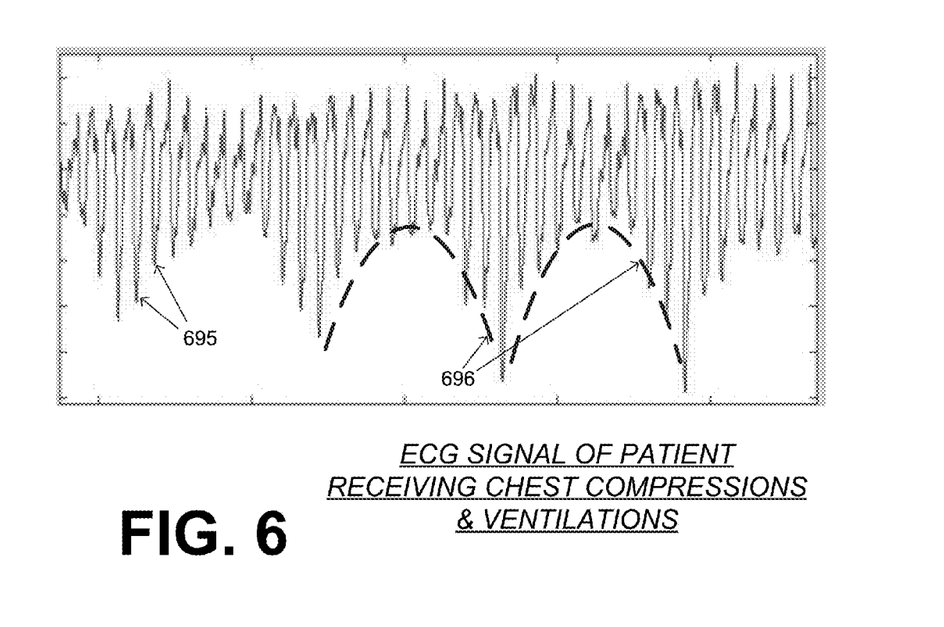
FIG. 6 is a time diagram of a patient ECG signal who is receiving chest compressions and ventilations.

FIG. 6 is a time diagram of an ECG signal of a patient who is receiving chest compressions and ventilations, such as patient 482 of FIG. 4. The horizontal axis represents time, and the vertical axis represents signal amplitude. In the example of FIG. 6, the patient is in ventricular fibrillation ("VF"), but the ECG signal is obscured by artifact. Compression artifact shows up as roughly sine-wave components 695 that occur slightly more than once per second. Ventilation artifact shows up as modulations 696 of the compression artifact. In this diagram, the ventilation artifact has a period of about 6 seconds.

Figure 7:
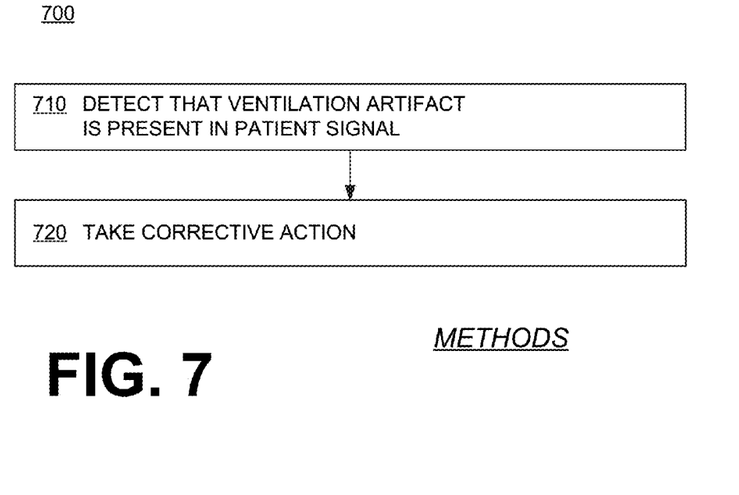
FIG. 7 is a flowchart for illustrating methods according to embodiments.

FIG. 7 shows a flowchart 700 for describing methods according to embodiments. The methods of flowchart 700 may also be user 480 who cares for patient 482.

According to an operation 710, it is detected that ventilation artifact is present in a signal of the patient. Detecting can be performed in a number of ways. In some embodiments, detecting is performed by inspecting a visual representation of the patient signal, such as that of FIG. 6. Characteristics of ventilation artifact may be recognized. In other embodiments, detecting is performed by an automatic analysis of the patient signal. For example, the analyzed patient signal is one of an ECG signal and an impedance signal of the patient. In other embodiments, detecting is performed by viewing a correlation of an airway signal of the patient, with another signal of the patient. The airway signal can be a capnography signal, an airway pressure signal, or an air flow signal. The other signal can be the ECG signal or the impedance signal. The correlation may reveal the presence of the ventilation artifact in the patient signal.

According to another operation 720, a corrective action is taken, responsive to so detecting at operation 710. The corrective action can be taken in a number of ways. In some embodiments, the corrective action includes discontinuing an operation of a ventilator that presumptively has caused the ventilation artifact. The discontinuing can be indefinite, or merely the beginning of a pause, after which the ventilator operation is resumed. In the example of FIG. 4, user 482 would discontinue operation of ventilator 486. In other embodiments, the corrective action includes discontinuing manual ventilations, such as from one of the rescuers. In other embodiments, the corrective action includes causing an augmented filter to be applied to the patient signal, so that the ventilation artifact is removed. In the example of FIG. 4, user 482 might enter the appropriate inputs for filter mechanism 425 or for another filter to be applied to the patient signal.

The above-mentioned devices and/or systems perform functions, processes and/or methods, as described in this document. The functions, processes and/or methods may be implemented by one or more devices that include logic circuitry. Such a device can be alternately called a computer, a device, and so on. It may be a standalone device or computer, such as a general purpose computer, or part of a device that has one or more additional functions. The logic circuitry may include a processor that may be programmable for a general purpose, or dedicated, such as a microcontroller, a microprocessor, a Digital Signal Processor (DSP), etc. The logic circuitry may also include storage media, such as a memory. Such media include but are not limited to volatile memory, non-volatile memory (NVM), read only memory (ROM); random access memory (RAM); magnetic disk storage media; optical storage media; smart cards, flash memory devices, etc. Any one of these storage media could be a non-transitory computer-readable medium. These storage media, individually or in combination with others, can have stored thereon programs that the processor may be able to read, and execute. More particularly, the programs can include instructions in the form of code, which the processor may be able to execute upon reading. Executing is performed by physical manipulations of physical quantities, and may result in the functions, processes and/or methods to be performed. In addition, these storage media may store data.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs. A method is now described.

Figure 8:
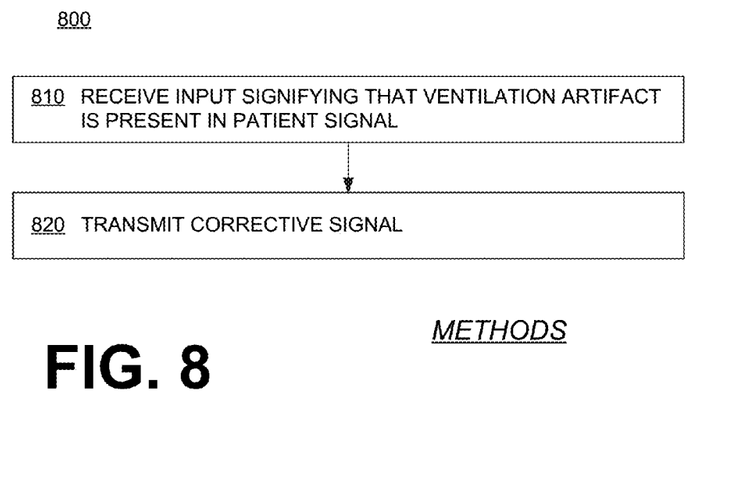
FIG. 8 is a flowchart for illustrating methods according to embodiments.

FIG. 8 shows a flowchart 800 for describing methods according to embodiments. The methods of flowchart 800 may also be practiced by embodiments described above, such as medical device 400.

According to an operation 810, an input is received, which signifies that ventilation artifact is present in a signal of the patient. The input may be received in any number of ways. In some embodiments, the input is received from a user, such as user 480. In some embodiments, a correlation is performed of an airway signal of the patient with another signal of the patient. The input can be received responsive to an outcome of the correlation. In other embodiments the input may be received by a frequency analysis of a patient signal such as the ECG signal or impedance waveform. In yet other embodiments the input by be received by a time-domain analysis of the ECG signal. As seen in FIG. 6 amplitude modulation of the ECG signal at the ventilation frequency is characteristic of ventilation artifact.

According to another operation 820, a corrective signal is transmitted responsive to the received input. The corrective signal can be taken in a number of ways. In some embodiments, the corrective signal causes a prompt to be output to a user, such as user 480. The prompt can be audible or visible, and can be to the effect of pausing or discontinuing an operation of a ventilator that presumptively has caused the ventilation artifact, such as ventilator 486. The prompt may positively indicate either the presence or absence of ventilation artifact. Indicating the absence of ventilation artifact is important because it tells the operator that they may be able to trust the results of a comb filter to remove compression artifact. In some embodiments, the corrective signal can be transmitted to a ventilator whose operation presumptively has caused the ventilation artifact, such as ventilator 486. The corrective signal can thus cause the ventilator operation to be discontinued. In other embodiments, the corrective signal includes causing an augmented filter to be applied to the patient signal, so that the ventilation artifact is removed. In the example of FIG. 4, the corrective signal might cause filter mechanism 425 or another filter to be applied to the patient signal.

According to another, optional operation, a record can be caused to be created. The record can be about the input, the corrective signal, and so on. The created record can be added to the patient record.

Filtering is now described in more detail. Filtering may include using filter mechanism 425 and/or one or more augmented filters, as already mentioned above.

Filtering is intended to be applied to a received patient signal, so as to result in a filtered signal. Compared to the received patient signal, the filtered signal will lack artifacts that have been removed by the filtering. As seen in FIG. 5, the source of the artifacts is component 595 from the chest compressions at frequency Fc, and component 596 from the ventilations at frequency Fv.

In certain embodiments, filter mechanism 425 includes a comb filter. The comb filter may be non-adaptive. In other embodiments, filter mechanism 425 includes a plurality of notch filters. Each of the notch filters may be non-adaptive. One having ordinary skill in the art will readily recognize that various other filter mechanisms may be used in addition to, or in place of, a comb filter or notch filters.

Certain conventional CPR artifact filters may be adaptive in nature. As used herein, an adaptive filter generally refers to a filter whose transfer function is dependent on the patient signal. An adaptive filter may adjust its filter coefficients, center frequency, roll-off, notch width, Q, or other characteristic based on the patient signal. In contrast, non-adaptive filters according to embodiments generally use predetermined coefficients that may precisely set the transfer function independent of the patient signal.

It is possible that a device incorporating this invention may include multiple non-adaptive filters. The appropriate filter may be selected based on patient signal characteristics, such as the frequency content of the ECG signal or impedance signal. Alternatively, the appropriate filter may be selected by communication with the mechanical chest compression device, or through a user input selection.

As for removal of artifacts, some drawings are now presented initially to show their nature. The first few drawings address only the artifact due to the chest compressions. Then the artifact due to the added ventilation will also be addressed.

Figure 9:
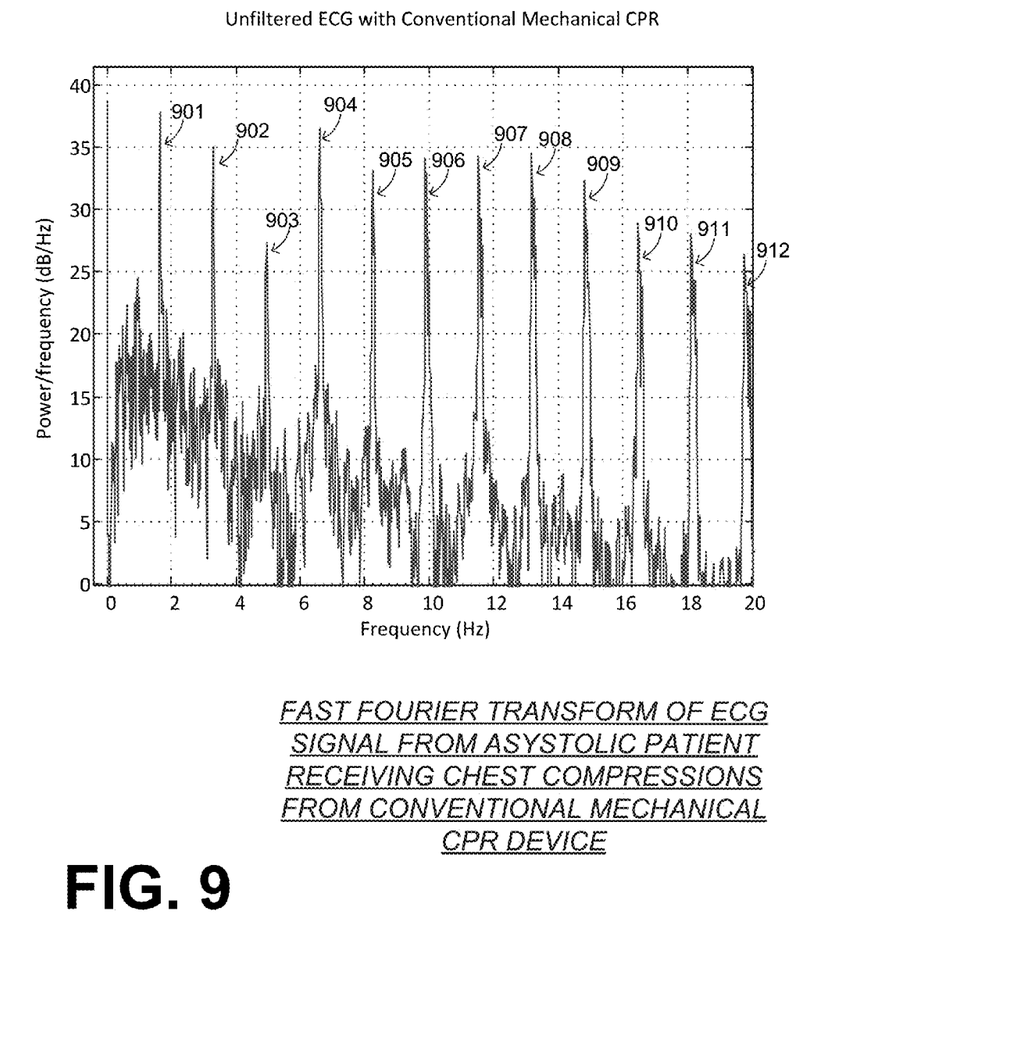
FIG. 9 is a graphical illustration of a fast Fourier transform of an ECG signal of an asystolic patient receiving chest compressions from a conventional mechanical chest compression device.

FIG. 9 is a graphical illustration of a fast Fourier transform of an ECG signal of an asystolic patient who is receiving only chest compressions. The compressions are from a machine that does not have precise frequency control. As can be seen from the illustrated example, the ECG signal generally contains only artifacts, because the patient has no active cardiac signal. Multiple spectral peaks are evident, with the fundamental frequency component 901 of the chest compressions appearing at 1.67 Hz, and other frequency components 902, 903, . . . , 912 representing harmonic frequencies. That, even though the source of the artifacts is a component 595 at a single frequency Fc, here 1.67 Hz. Artifact from ventilations 496 would also appear in components at a fundamental frequency Fv and higher harmonics.

The width of the spectral peaks in FIG. 9 varies from approximately 0.15 Hz at the fundamental frequency, up to approximately 0.5 Hz for the $6^{th}$ harmonic (10 Hz). At first sight, removing the CPR artifact from the illustrated signal would necessarily remove much of the cardiac signal, due to the requirement of a relatively wide filter, and would thus cause distortion that impacts adversely the patient signal that is to be extracted.

Signals corresponding to manual CPR or conventional mechanical CPR devices generally have only broad spectral peaks, and the locations of such peaks are typically not precisely controlled. The fundamental frequency may vary from one device to another, or from one application to another. For example, the fundamental frequency may vary from 1.4 Hz to 1.7 Hz. Such variation generally prevents application of a non-adaptive filter, e.g., a comb filter, with a narrow stop band.

Conventional CPR artifact filters have been unsuccessful at removing CPR artifacts, in part, because they typically focus on removing the fundamental frequency while paying little, if any, attention to the harmonic frequencies. In the example illustrated by FIG. 9, component 912 of the 12$^{th}$ harmonic is only about 11 dB down from component 901 of the fundamental frequency. In order to produce a clean ECG signal, CPR artifacts usually need to be attenuated by at least 20 dB, and possibly as much as 40 dB. In order to clean up the signal, frequencies up to at least the 12$^{th}$ harmonic must typically be removed.

Figure 10:
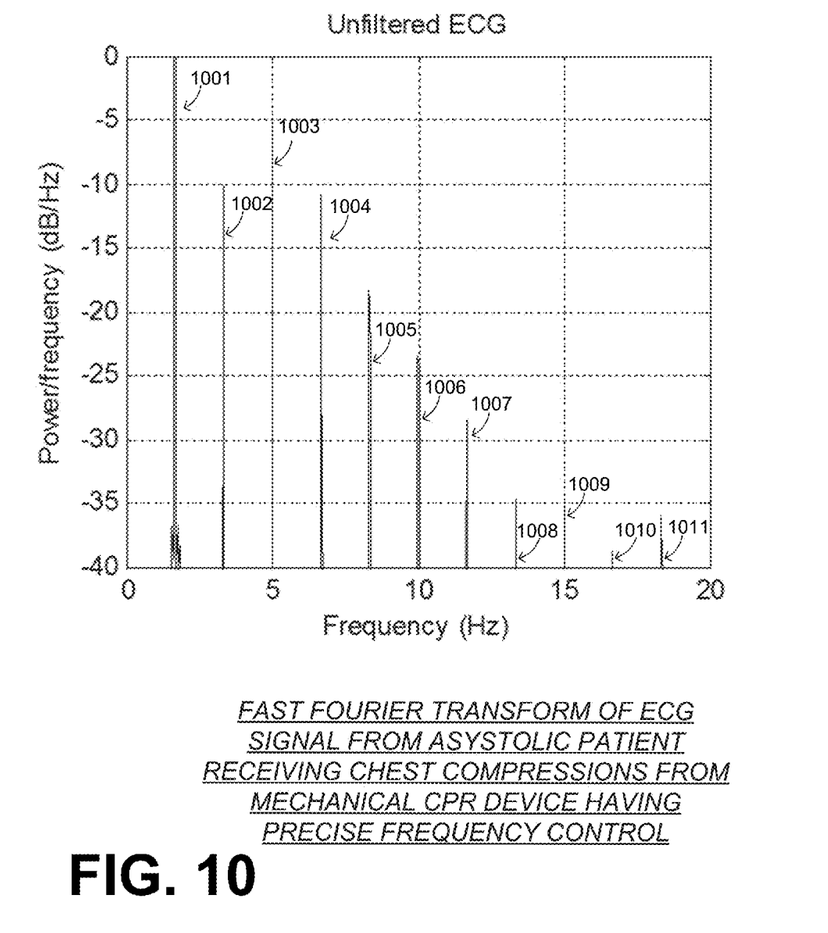
FIG. 10 is a graphical illustration of a fast Fourier transform of an ECG signal from an asystolic patient receiving chest compressions from a mechanical chest compression device having precise frequency control according to embodiments.

FIG. 10 is a graphical illustration of a fast Fourier transform of an ECG signal from an asystolic patient who is receiving only chest compressions according to embodiments. The compressions are from a machine that has precise frequency control. The spectral peaks of the artifacts generated by this device are typically very narrow, e.g., less than 0.1 Hz wide. This narrow spectral content enables the ECG signal to be separated from chest compression artifact. As with the signal of FIG. 9, beyond a component 1001 of the fundamental frequency, multiple components 1002, 1003, . . . , 1011 of frequency harmonics are present in the signal of FIG. 10. It will be noted that the 5$^{th}$ harmonic is less than 20 dB down, and the 11$^{th}$ harmonic is less than 40 dB down. In order to clean up the signal, harmonics up to at least the 5$^{th}$ harmonic, and possibly as high as the 11$^{th}$ harmonic, should be removed.

Figure 11:
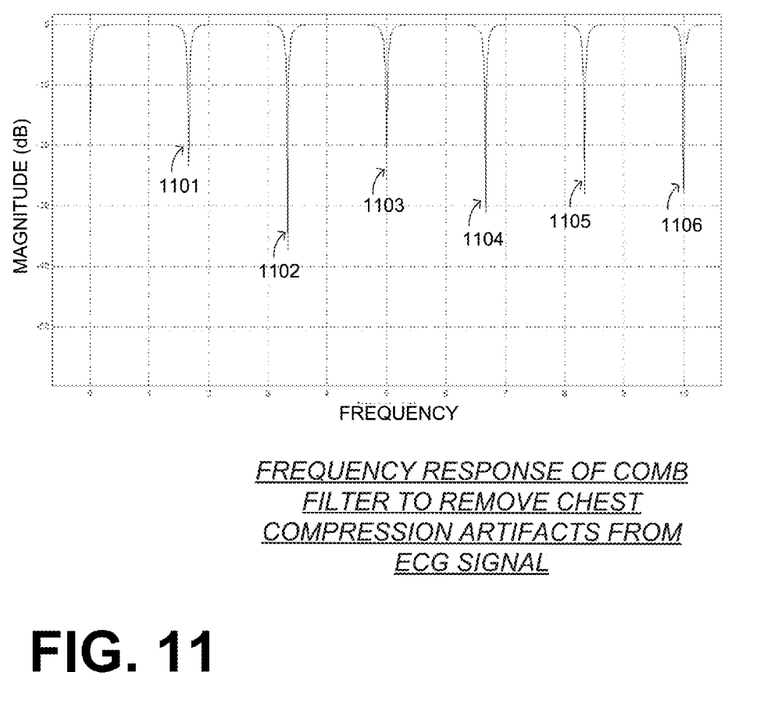
FIG. 11 is a graphical illustration of the frequency response of a comb filter suitable for removing chest compression artifacts from an ECG signal according to embodiments.

FIG. 11 is a graphical illustration of the frequency response of a comb filter, which attenuates bands 1101, 1102, . . . , 1006. A comb filter intrinsically removes the component at a fundamental frequency, and at all the harmonics. As such, the comb filter of FIG. 11 would be applicable for removing artifacts from compressions 495, or ventilations 496.

The comb filter can be a high-Q comb filter, e.g., Q=16, suitable for removing chest compression artifacts from an ECG signal according to embodiments. If the Q is set relatively high, e.g. 16, the filter will surgically remove the artifact frequencies and leave the other frequencies relatively untouched.

In general, high-Q filters are more frequency-selective than low-Q filters. For example, a comb filter having Q=16 will generally have a 3 dB notch width of about 0.1 Hz, whereas a comb filter having Q=4 will typically have a 3 dB notch width of about 0.5 Hz. A filter having Q=2 has approximately a 3 dB notch width of about 1 Hz and usually removes almost as much of the signal as it retains. A lower-Q filter will generally remove more artifacts from a signal than a high-Q filter but will also remove more of the signal itself. In addition, a low-Q filter tends to produce more ringing, which often provides additional distortion.

In order to effectively remove CPR artifacts resulting from application of a conventional chest compression device, a very low-Q filter is preferable. Assuming that at least 20 dB of attenuation is needed, even a filter having Q=2 would generally not be effective in removing the artifact from the signal due to the spectral peaks of the artifact being too tall and too broad.

Because the spectral content of a mechanical CPR device according to embodiments is generally extremely narrow, a high-Q filter may be used to remove the compression artifact and retain the cardiac ECG signal with little distortion. Because a mechanical CPR device according to embodiments generally produces compressions at a precisely known frequency, the artifact may be filtered using a non-adaptive filter. Combining these two aspects (narrow frequency content and precise frequency control) according to embodiments may thus enable a high-Q comb filter to be used as an effective filter for removing CPR artifacts from the patient signal.

The following is a Z transform of a suitable comb filter:

$$H(z) = \frac{a(z^{-1} - z^{-n})}{1 - bz^{-n}}$$

where "a" is a gain constant, "b" sets the filter Q, and "n" is an integer that sets the notch frequencies. The Q of this filter may be set by a single coefficient, the constant "b." For example, b=0.82 for a Q of 16. The value of "n" and the sample frequency may be set to locations of the comb notch frequencies. In situations where n=75 and the sample rate is 125 Hz, for example, the notch frequencies would be 1⅔ Hz, 3⅓ Hz, 5.0 Hz, etc.

A comb filter generally introduces very little signal delay. The signal is typically delayed by only one sample. For example, at 125 Hz, the delay would be only 8 milliseconds. From a user's standpoint, this delay is imperceptible. This is in contrast to certain filter structures, such as finite impulse response (FIR) filters, that can delay the signal by a second or more. Such a delay could lead to a misalignment between the filtered ECG and other signals, such as the unfiltered ECG or an invasive blood pressure waveform, which could be confusing to the user. Alternatively or in addition thereto, a collection of narrow notch filters, e.g., one filter for the fundamental frequency and one for every harmonic that needs to be removed, may be used. This small delay may make a comb filter particularly suitable for an ECG display, in which signal delays or misalignment with other monitoring parameters may be objectionable.

Figure 12:
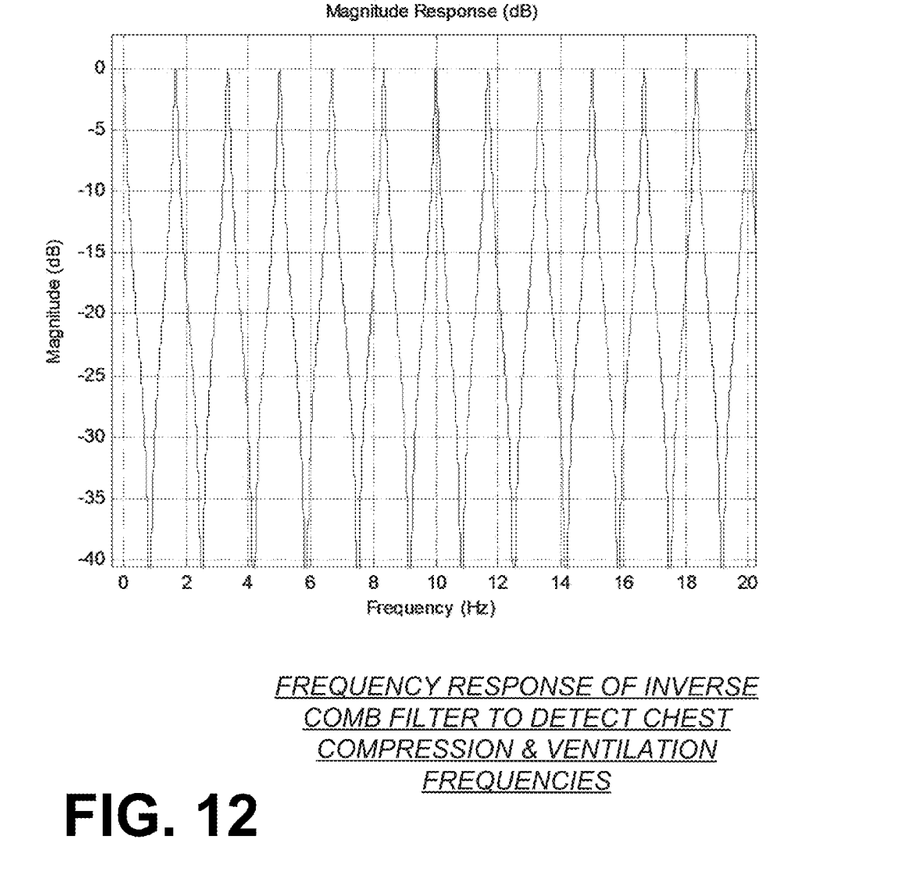
FIG. 12 is a graphical illustration of the frequency response of an inverse comb filter suitable for removing chest compression artifacts from an ECG signal according to embodiments.

FIG. 12 is a graphical illustration of the frequency response of an inverse comb filter, which may be suitable for detecting chest compression artifacts from an ECG signal according to embodiments. An inverse comb filter is generally similar to a comb filter except that it passes the comb frequencies instead of rejecting them. Such an inverse comb filter may be particularly suitable for detection of mechanical compressions delivered at certain rates, e.g., 100 compressions/minute.

Figure 13:
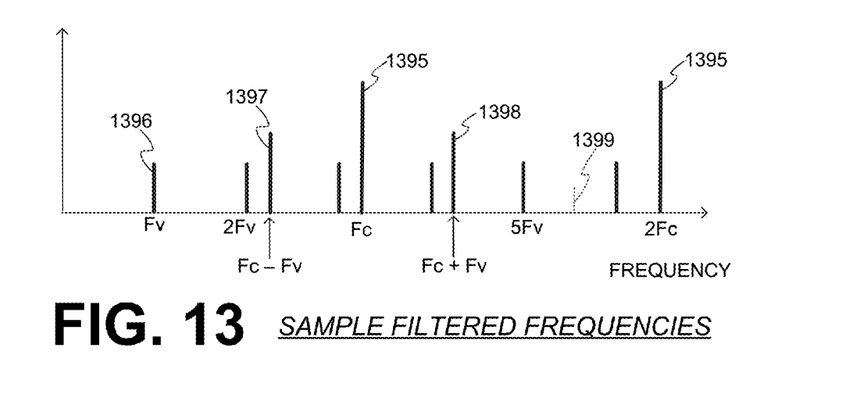
FIG. 13 is a diagram showing sample frequencies that have artifacts, and which are rejected by filters and filtering according to embodiments.

FIG. 13 is a diagram showing, as heavy dark lines, sample frequencies that have artifacts, and which are rejected by filters, filter mechanisms, and filtering according to embodiments. In the diagram of FIG. 13, there is no meaning to the vertical dimension. Rather, similar frequency components are shown having equal heights for clarity. In addition, the diagram of FIG. 13 is somewhat idealized for comprehension, in that each frequency component is shown as having practically no width.

The components include a fundamental frequency component 1396 at frequency Fv, and also higher harmonics of Fv. Only five such higher harmonics are shown. The components also include a fundamental frequency component 1395 at frequency Fc, and also higher harmonics of Fc. Only one such higher harmonic is shown. Typically, the values frequencies Fv and Fc would have a ratio of 1:10. In FIG. 13, however, the ratio is shown artificially as only 1:3.25 for clarity of the mixing that is now described.

Artifacts may exist also in third frequencies such as Fc+Fv, and Fc−Fv, and even harmonics of those. In other words, frequencies Fc and Fv mix, and create artifact in the patient signal also in these third frequencies. In FIG. 13, a component 1397 is shown at a third frequency Fc−Fv, and a component 1398 is shown at another third frequency Fc+Fv. Mixing happens when compressions 495 and ventilations 496 are received concurrently by patient 482. Artifacts are an example of noise.

Filters and filtering according to the invention reject, do not pass, or filter out at least some of the above mentioned frequencies. However, they admit or pass other frequencies between them, such as a component 1399.

For example, the noise spectrum resulting from mixing, and which would have to be filtered, may include filtering 0.167 Hz (plus harmonics), 1.667 Hz (plus harmonics), as well as 1.667 Hz+0.167 Hz=1.834 Hz and 1.667 Hz−0.167 Hz=1.5 Hz. The same thing happens for every harmonic of 1.667 Hz and 0.167 Hz.

Figure 14:
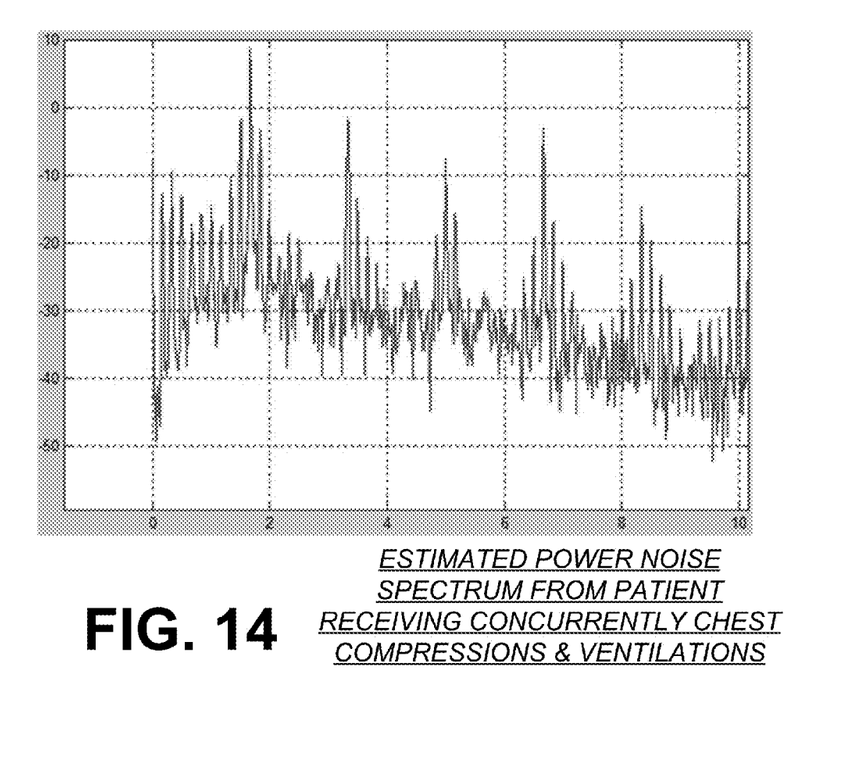
FIG. 14 is a graphical illustration of an estimated power noise spectrum in a patient signal of patient receiving concurrently chest compressions and ventilations according to embodiments.

FIG. 14 is a graphical illustration of an estimated power noise spectrum in a patient signal of patient receiving concurrently chest compressions and ventilations according to embodiments. The horizontal axis indicates frequency in Hz. The vertical axis indicates power/frequency in dB/Hz.

In FIG. 14, Fc and Fv have values as in the example above, plus each component has a width, unlike in the idealized diagram of FIG. 13. The spectrum of FIG. 14 is strikingly different from that of FIG. 10. A filter that rejects the artifact noise frequencies of FIG. 10 will not succeed in rejecting the artifact noise frequencies of FIG. 14. This problem tends to occur when ventilation artifact mixes with compression artifact, such as when ventilations are received concurrently with compressions. Compression artifact alone can be removed with a comb filter that covers only one fundamental and its harmonics. However, when ventilation artifact is mixed with the compression artifact, the comb filter for the compression artifact alone may not be enough. Ventilation artifact alone generally falls outside the ECG frequency band, and thus can be removed using standard filtering techniques.

It is desirable to precisely control the ventilation, so that it produces artifacts of known frequencies, as was indicated in FIG. 13. The artifact from a hand-ventilated patient is hard to remove because the ventilation rate is not precisely controlled. If the ventilation rate was precisely controlled and it was known in advance, it is possible that the artifact could be removed with a comb filter, similar to one used for ECG alone.

It is important that the ventilation rate be chosen to work well with the monitor, and that the monitor knows the ventilation rate. If the ventilation rate were set to 0.167 Hz, then a 750 tap comb filter would remove the ventilation artifact from the ECG signal (assuming a 125 Hz sample rate). In fact, it would remove the 0.167 Hz ventilation fundamental and all of its harmonics (i.e. 0.334 Hz, 0.50 Hz, 0.668 Hz, etc.). While a 750 tap comb filter may notch out many frequencies (i.e. all multiples of 0.167 Hz) within the ECG pass band, it may have an undesirable impact on the ECG.

A somewhat less invasive technique would be to use a set of notch filters chosen to remove the specific frequencies of interest. The main frequencies of interest are those at multiples of the compression frequency Fc+/− the ventilation frequency Fv. For example, with a compression frequency of 1.667 Hz and a ventilation frequency of 0.167 Hz, one might choose to notch out 1.5 Hz, 1.834 Hz, 3.167 Hz, 3.5 Hz and so forth.

Figure 15:
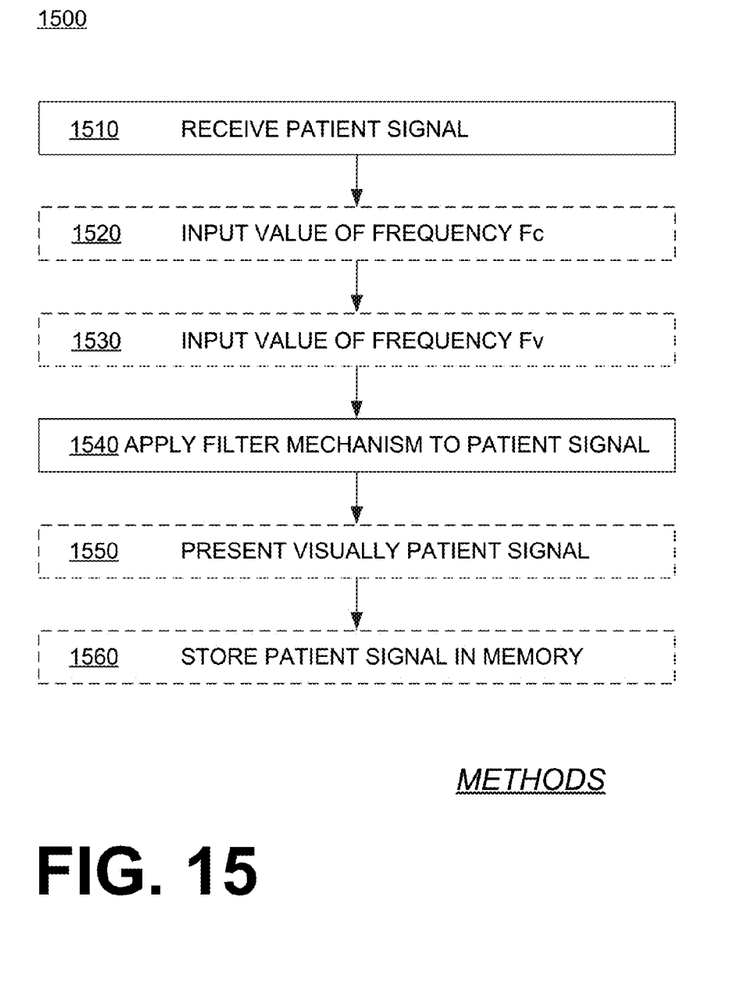
FIG. 15 is a flowchart for illustrating methods according to embodiments.

FIG. 15 shows a flowchart 1500 for describing methods according to embodiments. The methods of flowchart 1500 may also be practiced by embodiments described above, such as device 400, processor 430, a monitor defibrillator, a computer performing post-event review, and so on.

According to an operation 1510, a patient signal is received. The patient signal can be, for example, an ECG signal, an impedance signal, and so on. The patient signal may be received from a patient who is receiving chest compressions at a frequency Fc from a mechanical chest compression device, and also receiving ventilations at frequency Fv from a ventilator.

According to another, optional operation 1520, a value of frequency Fc is input. This may be accomplished in a number of ways, according to embodiments. An identification of the mechanical chest compression device may be inputted, by the user or by sensing the device, or by transmission from the device, such as wireless transmission. Then the frequency Fc can be looked up from the identification of the mechanical chest compression device. Or an indication may be received about the frequency Fc, such as from a user via an interface, or by transmission from the mechanical chest compression device. Or the chest compressions can be detected and analyzed, and the frequency Fc can be input from the analysis.

According to another, optional operation 1530, a value of frequency Fv is input. This may be accomplished in a number of ways, according to embodiments. An identification of the ventilator may be inputted, by the user or by sensing the ventilator, or by transmission from the ventilator, such as wireless transmission. Then the frequency Fv can be looked up from the identification of the ventilator. Or an indication may be received about the frequency Fv, such as from a user via an interface, or by transmission from the ventilator. Or the ventilations can be detected and analyzed, and the frequency Fv can be input from the analysis.

According to another operation 1540, at least one filter mechanism may be applied to the patient signal. The filter mechanism may be applied in any way, such as automatically, responsive to an input by a user, and so on. The receiving of the patient signal and applying the filter mechanism can be performed by a device in the field or afterwards, as part of a post-event review.

The result of applying the filter mechanism may be that artifacts will be substantially removed from the patient signal, at a) the frequency Fc, b) a higher harmonic of the frequency Fc, and c) a third frequency substantially equaling the frequency Fc plus or minus the frequency Fv, such as component 1397 or 1398. In addition, the result will be that the filter mechanism will substantially pass other frequencies, such as component 1399. These other frequencies can be between the frequency Fc and the higher harmonic, and between the frequency Fc and the third frequency.

The above mentioned frequency components are at a minimum. Preferably, the filter mechanism will substantially reject more frequencies, such as at least two more frequencies that are additional higher harmonics of the frequency Fc.

According to another, optional operation 1550, the patient signal is visually presented to a user, via a display that is part of a user interface. The displayed patient signal could be a version with the artifacts substantially removed.

According to another, optional operation 1560, a version of the patient signal is stored in a memory. The version could be with the artifacts removed, or not removed.

According to another, optional operation, an impedance signal of the patient is monitored. Return of spontaneous circulation (ROSC) is detected by applying a signal-averaging filter to the impedance signal.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

Another strategy is to avoid creating ventilation artifact in the first place by using a ventilation strategy such as continuous oxygen insufflation. Continuous oxygen insufflation is a method of providing oxygen to the patient that does not move a large volume of air in and out of the lungs. Instead, a small amount of oxygen is fed in to the airway on a continuous basis. Because the oxygen flow is not periodic it will not mix with the ECG signal.

This description includes one or more examples, but that does not limit how the invention may be practiced. Indeed, examples or embodiments of the invention may be practiced according to what is described, or yet differently, and also in conjunction with other present or future technologies.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment, extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and sub-combinations of elements, features and steps or operations, which are regarded as novel and non-obvious. Additional claims for other such combinations and subcombinations may be presented in this or a related document.

What is claimed is:

1. An external device, comprising:
a housing; and
a processor within the housing configured to:
receive a patient signal generated from a patient while the patient is receiving chest compressions at a frequency Fc from a mechanical chest compression device, and while the patient is also receiving ventilations at a frequency Fv from a ventilator, the frequency Fv having a value between $1/20^{th}$ of the frequency Fc and $1/4$ of the frequency Fc, and
cause to be applied at least one filter mechanism to the patient signal to substantially remove from the patient signal artifacts at the frequency Fc and at the frequency Fv, while substantially passing the patient signal at other frequencies between the frequency Fv and the frequency Fc.

2. The device of claim 1, in which
the patient signal is an ECG signal.

3. The device of claim 1, in which
the patient signal is an impedance signal.

4. The device of claim 1, further comprising:
an energy storage module within the housing for storing an electrical charge; and
a defibrillation port for guiding via electrodes the stored electrical charge to the patient.

5. The device of claim 1, in which
a value of the frequency Fc is input in the device.

6. The device of claim 5, in which
the value of the frequency Fc is input by being looked up from an inputted identification of the mechanical chest compression device.

7. The device of claim 5, in which
the value of the frequency Fc is input by detecting and analyzing the chest compressions.

8. The device of claim 1, in which
a value of the frequency Fv is input in the device.

9. The device of claim 8, in which
the value of the frequency Fv is input by being looked up from an inputted identification of the ventilator.

10. The device of claim 8, in which
the value of the frequency Fv is input by detecting and analyzing the ventilations.

11. The device of claim 1, in which
the processor is configured to apply the filter mechanism responsive to an input by a user.

12. The device of claim 1, in which
the filter mechanism further substantially removes from the patient signal artifacts at the frequency 2Fv.

13. The device of claim 1, in which
the filter mechanism further substantially removes from the patient signal artifacts at two more frequencies that are additional higher harmonics of the frequency Fc.

14. The device of claim 1, further comprising:
a display in connection with the housing, and
in which the processor is further configured to cause the display to present a version of the patient signal with the artifacts substantially removed.

15. The device of claim 1, further comprising:
a memory, and
in which the processor is further configured to store in the memory a version of the patient signal with the artifacts substantially removed.

16. The device of claim 1, in which
the filter mechanism comprises a comb filter.

17. The device of claim 1, in which
the filter mechanism has a Q value of no less than 4.

18. The device of claim 1, in which
the filter mechanism comprises a plurality of notch filters.

19. The device of claim 18, in which
the plurality of notch filters have a 3 dB notch width of no more than 0.5 Hz.

20. The device of claim 1, in which
the filter mechanism includes a non-adaptive filter.

21. The device of claim 1, in which
the patient signal is an impedance signal, and
the processor is further configured to detect a return of spontaneous circulation from the impedance signal.

22. The device of claim 1, in which
the processor is further configured to monitor an impedance signal of the patient, and to further detect a return of spontaneous circulation from the impedance signal.

* * * * *